(12) United States Patent  
Taniguchi et al.

(10) Patent No.: US 8,227,263 B2
(45) Date of Patent: Jul. 24, 2012

(54) PROCESS FOR PRODUCING POLYMER PARTICLES

(75) Inventors: Tatsuo Taniguchi, Chiba (JP); Akihiro Mizuno, Chiba (JP); Tokio Sawai, Tokyo (JP); Hiroyuki Tsubota, Tokyo (JP)

(73) Assignees: Mitsubishi Chemical Medience Corporation, Tokyo (JP); National University Corporation Chiba University, Chiba (JP)

( * ) Notice: Subject to any disclaimer, the term of this patent is extended or adjusted under 35 U.S.C. 154(b) by 484 days.

(21) Appl. No.: 12/445,881

(22) PCT Filed: Oct. 16, 2007

(86) PCT No.: PCT/JP2007/070189
§ 371 (c)(1),
(2), (4) Date: Apr. 16, 2009

(87) PCT Pub. No.: WO2008/047798
PCT Pub. Date: Apr. 24, 2008

(65) Prior Publication Data
US 2010/0304503 A1 Dec. 2, 2010

(30) Foreign Application Priority Data

Oct. 16, 2006 (JP) ................................ 2006-281840

(51) Int. Cl.
*G01N 33/546* (2006.01)
(52) U.S. Cl. ........................................ 436/535; 436/534
(58) Field of Classification Search ........................ None
See application file for complete search history.

(56) References Cited

U.S. PATENT DOCUMENTS

| 4,061,466 | A | 12/1977 | Sjoholm et al. |
| 4,511,478 | A | 4/1985 | Nowinski et al. |
| 4,609,707 | A | 9/1986 | Nowinski et al. |
| 4,711,840 | A | 12/1987 | Nowinski et al. |
| 4,752,638 | A | 6/1988 | Nowinski et al. |
| 4,843,010 | A | 6/1989 | Nowinski et al. |
| 5,166,077 | A | 11/1992 | Kihara et al. |

FOREIGN PATENT DOCUMENTS

| JP | 05-247108 | | 9/1993 |
| JP | 5-247108 | A | 9/1993 |
| JP | 08-059715 | | 3/1996 |
| JP | 8-59715 | A | 3/1996 |
| JP | 2004-141116 | A | 5/2004 |
| JP | 2004-226395 | A | 8/2004 |
| JP | 2006-145256 | | 6/2006 |
| JP | 2006-145256 | A | 6/2006 |
| JP | 2007-155691 | A | 6/2007 |
| WO | 02/02647 | | 1/2002 |

OTHER PUBLICATIONS

Akihiro Mizuno et al, "Preparation of Polymer Latex Particles Supporting Proteins by Miniemulsion Polymerization," Polymer Preprints, Japan, May 10, 2007, vol. 56, No. 1, p. 1003, Abstract Only.*
Daisuke Kobayashi et al, Emulsion Polymerization of Styrene Under Indirect Ultrasonic Irradiation, Jan. 20, 2006, Kagaku Kogaku Ronbunshu, vol. 32, No. 1, pp. 88 to 92, Abstract Only.*
Hiroshi Sekiguchi et al, "Preparation of Polymer Particles Hybridized with Gold Colloids by Mini-Emulsion Polymerization," Polymer Preprints, Japan, May 10, 2006, vol. 55, No. 1, p. 1153, Abstract Only.*
International Search Report for PCT/JP2007/070189 dated Nov. 7, 2007.
Antonietti, M., et al "Polyreactions in miniemulsions," Prog. Polym. Sci., 2002, pp. 689-757, vol. 27, No. 4.
Ryuji Tomiyama, Rinsho Byori, "The Japanese Journal of Clinical Pathology", Aug. 2000, vol. 48(8), 2000, 760-763.

* cited by examiner

*Primary Examiner* — David A Saunders
(74) *Attorney, Agent, or Firm* — Heslin Rothenberg Farley & Mesiti P.C.

(57) ABSTRACT

A process for producing polymer particles having an antigen or an antibody introduced into the surface thereof, by carrying out miniemulsion polymerization using a monomer, a radical polymerization initiator, an emulsifier, and a hydrophobe in the presence of the antigen or antibody to thereby produce the polymer particles, is disclosed. According to the process, it is possible to provide a reagent for immunological analysis having an excellent detection sensitivity and capable of avoiding a nonspecific reaction which occurs in conventional methods.

7 Claims, 1 Drawing Sheet

PROCESS FOR PRODUCING POLYMER PARTICLES

This application is a 371 filing of PCT Application No. PCT/JP2007/070189 filed Oct. 16, 2007 and published in Japanese as WO 2008/047798 on Apr. 24, 2008, which claims the priority of Japanese Application No. 2006-281840 filed Oct. 16, 2006.

TECHNICAL FIELD

The present invention relates to a process for producing polymer particles having an antigen or an antibody introduced into the surface thereof, by the coexistence of the antigen or antibody in miniemulsion polymerization.

BACKGROUND ART

In the field of clinical diagnostic tests, various substances, which may be used as an index of diagnosis of diseases, in a large number of samples should be measured rapidly and accurately, and a rapid and accurate feedback of the results should be given to a treating room. In particular, immunological measurement based on an antigen-antibody reaction is widely used to accurately quantify a trace amount of a substance to be analyzed. In this regard, as a method for improving a detection sensitivity or accuracy, a latex agglutination method using particles made of a synthetic polymer such as polystyrene (so-called latex), in which an antigen or antibody specific for a substance to be analyzed is carried on the surface of the particles, is known. The latex agglutination method is a method for rapidly measuring a substance to be analyzed, by visually or optically detecting a degree of latex-particle-agglutination caused by a reaction of the substance to be analyzed with the antigen or antibody immobilized on the latex particles.

Further, a sandwich method, using magnetic particles instead of the latex particles, by trapping a substance to be analyzed with a first antibody immobilized on the magnetic particles, washing the magnetic particles accumulated by a magnet to remove unreacted substances and the like (so-called B/F separation), and adding a second antibody labeled with a signal-generating substance such as an enzyme or a fluorescent agent to thereby perform the analysis, is also widely used.

Almost all substances to be analyzed, which are quantified utilizing an antigen-antibody reaction, are generally trace components contained in biological samples, and therefore, accuracy in a low concentration range is important. However, because there is a case where an abnormally high level of a substance to be measured is observed in accordance with the progress of a disease, a reagent capable of accurately measuring from a low concentration range to a high concentration range is desired in the field of clinical diagnostic tests.

In methods using latex particles including the latex agglutination method and the sandwich method, it is essential to immobilize an antigen or antibody on the surface of the latex particles, and a method of physically or chemically immobilizing the antigen or antibody on the surface is used. For example, a method of directly immobilizing the antigen or antibody on the latex particles by physical adsorption, or a method of binding the antigen or antibody to the latex particles by a covalent binding via a functional group located on the surface of the latex particles, for example, an amino group, a carboxyl group, a mercapto group, a hydroxyl group, an aldehyde group, an epoxy group, or the like, is used.

However, an amount of the antigen or antibody capable of being carried on the latex surface is limited in these physically or chemically binding methods, and therefore, there is a limit to a measuring range or a detection sensitivity when the latex agglutination method or the sandwich method is carried out. That is, the properties (for example, a surface charge, a rate of introduced functional group, a distribution of particle size, or the like) of latex particles per se are not uniform among different lots or manufacturers, and therefore, even if a procedure of binding the antigen or antibody to latex particles is uniform, the properties of the resulting antibody-bound latex particles are not uniform. For example, in the methods of physically or chemically binding an antigen or antibody to the latex surface, not all amount of the antigen or antibody bind to the latex, and the unbound antigen or antibody is removed by washing after the binding procedure, or the bound antigen or antibody is often peeled from the latex by centrifugation or dispersion. That is, a change in the amount of an antigen or antibody bound affects a measuring range or a detection sensitivity.

Further, as a new problem recently raised, samples which cause a nonspecific reaction have been sometimes observed, as shown in non-patent reference 1. When an antigen or antibody is bound to the surface of latex particles, the antigen or antibody is structurally denatured, and the nonspecific reaction is caused by "a substance which binds to the denatured portion" contained in the samples. Due to the nonspecific reaction, the reliability of measured values is lost, and an accurate diagnosis cannot be made. This problem would not be solved by individual examinations as to an antigen or antibody, or latex particles, and is very difficult to solve.

[non-patent reference 1] Rinsho Byori (The Japanese Journal of Clinical Pathology), August 2000, vol. 48, no. 8, p. 760-763

DISCLOSURE OF THE INVENTION

Problems to be Solved by the Invention

The present inventors have conducted intensive studies of a method of binding an antigen or antibody to the surface of latex, instead of the above conventional physical or chemical binding methods, and found that when an antigen or antibody as a protein coexists in a synthesis of latex particles, latex particles in which the antigen or antibody is introduced into the surface of the latex particles can be obtained when the synthesis is completed. The present inventors further surprisingly found that the latex particles exhibit a higher reactivity to a substance to be analyzed in comparison with conventional reagents based on physical adsorption or the like, while the properties of the introduced antigen or antibody are maintained, and that the antigen or antibody introduced into the surface of the latex particles is not structurally denatured by the binding, and therefore, nonspecific reactions with samples which nonspecifically react with conventional reagents can be avoided. The present inventors found that a monomer can be polymerized under specific conditions, in a state that the antigen or antibody coexists in the synthetic reaction of latex particles, and completed the present invention.

An object of the present invention is to provide a novel process for producing polymer particles, which can provide a reagent for immunological analysis, having an excellent detection sensitivity and capable of avoiding the nonspecific reaction which occurs in conventional methods.

Means for Solving the Problems

The problem can be solved by the present invention, a process for producing polymer particles having an antigen or an antibody introduced into the surface thereof, characterized by comprising the step of carrying out miniemulsion polymerization using a monomer, a radical polymerization initiator, an emulsifier, and a hydrophobe in the presence of the antigen or antibody to thereby produce the polymer particles.

The present invention relates to a polymer particle having a protein introduced into the surface thereof, obtainable by the process.

According to a preferred embodiment of the present invention, the polymerization reaction is carried out at low temperature (more preferably at 0 to 40° C.) in the miniemulsion polymerization.

According to another preferred embodiment of the present invention, the radical polymerization initiator is a redox initiator, more preferably a combination of ascorbic acid and $H_2O_2$.

According to still another preferred embodiment of the present invention, the emulsifier is a surfactant, more preferably a polymeric surfactant having a polyethylene glycol chain.

According to still another preferred embodiment of the present invention, the hydrophobe is hexadecane or polystyrene.

Further, the present invention relates to:
[1] a reagent for immunological analysis, comprising a suspension of latex particles having an antigen or an antibody specific for a substance to be analyzed introduced into the surface of the latex particles, produced by polymerizing a monomer in the presence of the antigen or antibody to thereby synthesize the latex particles,
[2] a method for immunological analysis, comprising the step of bringing, in a liquid, (1) a sample suspected of containing a substance to be analyzed, into contact with (2) latex particles having an antigen or an antibody specific for the substance introduced into the surface of the latex particles, produced by polymerizing a monomer in the presence of the antigen or antibody to thereby synthesize the latex particles,
[3] the method of [2], further comprising the step of optically analyzing a degree of latex-particle-agglutination caused by an antigen-antibody reaction, after the contacting step, and
[4] the method of [2], further comprising, after the contacting step, the step of separating the latex particles from the liquid, and optically analyzing the substance to be analyzed bound to the latex particles, or the substance to be analyzed remaining in the liquid.

Effects of the Invention

According to the present invention, novel polymer particles, which can provide a reagent for immunological analysis, having an excellent detection sensitivity and capable of avoiding the nonspecific reaction which occurs in conventional methods, can be provided.

BEST MODE FOR CARRYING OUT THE INVENTION

Figure 1:
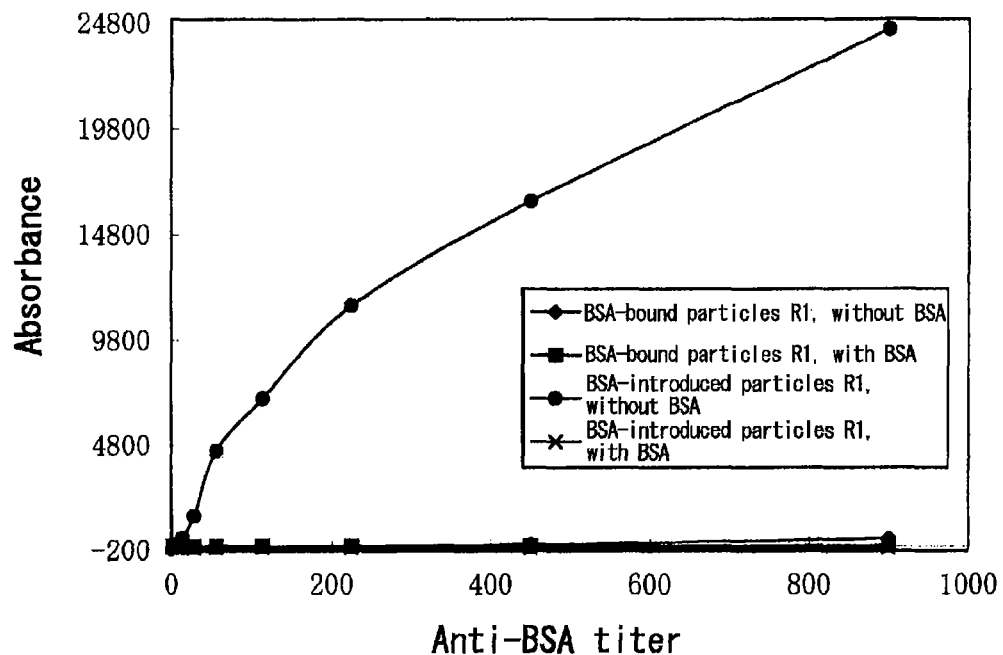
FIG. 1 is a graph showing the results obtained by measuring 2-fold-diluted series of a standard solution of an anti-BSA antibody, using a reagent of the present invention containing BSA-introduced latex particles, or a conventional reagent containing BSA-bound latex particles.

The process of the present invention is characterized by the coexistence of an antigen or an antibody in the process of miniemulsion polymerization. According to the process of the present invention, polymer particles (particularly, latex particles) having the antigen or antibody introduced into the surface thereof (hereinafter referred to as the partner-introduced polymer particles) can be produced.

The process of the present invention can be carried out in a fashion similar to conventional miniemulsion polymerization (for example, M. Antonietti, K. Landfester, Prog. Polym. Sci., 2002, 27, 689-757, and J. M. Asua, Prog. Polym. Sci., 2002, 27, 1283-1346), except that an antigen or antibody coexists in the polymerization reaction.

Conventional miniemulsion polymerization may comprise, but is by no means limited to, the steps of, for example, mixing a monomer, a radical polymerization initiator, an emulsifier, and a hydrophobe to prepare a mixture, shearing the mixture, and heating the sheared mixture to a polymerization initiation temperature to thereby carry out polymerization. In miniemulsion polymerization, after a monomer for polymerization is mixed with an emulsifier, a shearing step is carried out by, for example, supersonic radiation, to disrupt the monomer by a shearing force and form monomer droplets coated with the emulsifier. The monomer droplets are polymerized by heating the mixture to the polymerization initiation temperature of the radical polymerization initiator to obtain the polymer particles.

The antigen or antibody used in the present invention is not particularly limited, so long as it exhibits a surface activity, and an antigen or antibody which may be used in a latex method (for example, a latex agglutination method or a B/F separation using latex) is preferable. Whether or not a certain antigen or antibody exhibits a surface activity can be confirmed by a known method, such as a measurement of surface tension, or a measurement of a fluorescence spectrum using pyrene as a fluorescent probe. A preferred antigen or antibody used in the present invention exhibits an intensity ratio (I1/I3) of the first emission peak (I1) to the third emission peak (I3) of 0.5 to 1.6 (more preferably 0.6 to 1.5) in the fluorescence spectrum measurement using pyrene as a fluorescent probe. Examples of the antigen or antibody include various antibodies, receptors, enzymes, lipids, and sugar chains, more particularly, IgG, C-reactive protein (CRP), ferritin, β-2 microglobulin, α-fetoprotein (AFP), IgE, hepatitis B virus (HBs antibody or HBc antibody), D dimer, fibrin/fibrinogen degradation product (FDP), soluble fibrin (SF), plasmin-α2-plasmin inhibitor complex (PPI), prostate specific antigen (PSA), elastase 1, elastase XDP, thrombomodulin, and albumin (preferably serum albumin).

As the antibody, a monoclonal antibody or a polyclonal antibody may be used. The antibody may be used as an immunoglobulin molecule per se, or a fragment thereof, such as Fab, Fab', F(ab')$_2$, or Fv.

A monomer which may be used in conventional miniemulsion polymerization can be used in the present invention. Examples of the monomer include styrene, styrene derivatives (for example, chloromethylstyrene or sodium styrene sulfonate), acrylic acid or methacrylic acid, acrylic acid esters or methacrylic acid esters [for example, methyl (meta)acrylate, ethyl (meta)acrylate, butyl (meta)acrylate, hexadecyl (meta)acrylate,], and vinyl acetate.

A radical polymerization initiator which may be used in conventional miniemulsion polymerization can be used in the present invention, and may be, for example, a peroxide initiator, a persulfate initiator, an azo-initiator, or a redox initiator. The redox initiator is preferable in the present invention, because the polymerization reaction can be at low temperature. When the antigen or antibody which coexists in the polymerization reaction has physiological activities, a decrease in the physiological activities can be suppressed by performing the polymerization reaction at low temperature.

Examples of the peroxide initiator include benzoyl peroxide (BPO), di-t-butyl peroxide (DBPO), and ammonium peroxide. Examples of the persulfate initiator include potassium persulfate (KPS), ammonium persulfate (APS), and sodium persulfate (NPS). Examples of the azo-initiator include azobisisobutyronitrile (AIBN), dimethyl 2,2'-azobisisobutyrate (MAIB), 4,4'-azobis(4-cyanovaleric acid), and 2,2'-azobis(2,4-dimethylvaleronitrile).

Examples of the redox initiator include N,N,N',N'-tetramethylethylenediamine (TMEDA)/potassium persulfate (KPS), $FeSO_4$/KPS, $FeSO_4$/$H_2O_2$, and ascorbic acid (vitamin C)/$H_2O_2$. The combination of ascorbic acid/$H_2O_2$ is preferable, because a high conversion rate (for example, 75 to 98%) can be attained.

Various surfactants which may be used in conventional miniemulsion polymerization can be used as the emulsifier in the present invention, and may include anionic compounds, cationic compounds, and nonionic compounds. Examples of the nonionic compounds include a polymeric surfactant having a polyethylene glycol (PEG) chain, a long-chain alcohol, polyvinyl alcohol, and Brij 35 (PIERCE).

The polymeric surfactant having a polyethylene glycol (PEG) chain may be, for example, $CH_2=C(CH_3)COO(CH_2CH_2O)_nCH_3$ (n is an integer of 2 or more, preferably 2 to 100, more preferably 5 to 80, still more preferably 8 to 50, most preferably 9 to 23), more particularly, for example, $CH_2=C(CH_3)COO(CH_2CH_2O)_{23}CH_3$ [n=23; (product name) NK ester M-230G; Shin-nakamura Chemical Co. Ltd.], or $CH_2=C(CH_3)COO(CH_2CH_2O)_9CH_3$ [n=9; (product name) NK ester M-90G; Shin-nakamura Chemical Co. Ltd.]. Dispersion stability due to steric repulsion can be obtained by using the above polymeric surfactant as the emulsifier.

Examples of the long-chain alcohol include 1-pentanol and decanol.

A hydrophobe which may be used in conventional miniemulsion polymerization can be used in the present invention, and may be, for example, hexadecane, silsesquioxane, or a hydrophobic polymer (for example, polystyrene or polymethyl methacrylate). Hexadecane or polystyrene is preferable. When the hydrophobe is used, an increase in the heterogeneity of the particle size due to Oswald ripening can be suppressed, and therefore, monodispersed latex particles can be synthesized.

The reaction conditions in polymerization, such as a solvent, a mixing ratio, a temperature, or a reaction time, may be appropriately selected, for example, by carrying out a pilot experiment, in accordance with the type of a monomer and an antigen or antibody used, the average particle size of polymer particles to be synthesized, the amount of the antigen or antibody carried on the surface of the particles, or the like.

For example, with respect to 40 mmol of a monomer for polymerization (for example, a styrene monomer), an antigen or antibody [for example, bovine serum albumin, IgG, or $F(ab')_2$] at an amount of generally 0.01 to 5 g, preferably 0.02 to 2 g, more preferably 0.08 to 0.8 g; a radical polymerization initiator (for example, ascorbic acid or $H_2O_2$) at an amount of generally 0.01 to 4 mmol, preferably 0.02 to 2 mmol; and an emulsifier (for example, NK ester M-230G or NK ester M-90G) at an amount of generally 0.1 to 10 mmol, preferably 0.2 to 5 mmol, more preferably 0.4 to 4 mmol; may be used, respectively. The reaction time is generally 1 hour or more, preferably 3 to 48 hours, more preferably 4 to 24 hours. The reaction temperature is generally 0 to 80° C., preferably 0 to 60° C., more preferably 0 to 40° C.

According to the process of the present invention, latex particles having an antigen or antibody introduced into the surface of the latex particles can be produced.

In conventional latex particles, for example, an antigen or antibody is directly immobilized on the latex particles by physical adsorption, or an antigen or antibody is bound to the latex particles by a covalent binding via a functional group located on the surface of the latex particles, for example, an amino group, a carboxyl group, a mercapto group, a hydroxyl group, an aldehyde group, an epoxy group, or the like. In the antigen-or-antibody-introduced latex particles obtainable by the process of the present invention, the antigen or antibody is carried on the surface of the latex by embedding part of the antigen or antibody into the latex particles.

When latex particles are produced by miniemulsion polymerization carried out at low temperature, as a method of introducing a coexisting antigen or antibody into latex particles in the synthesis of the latex particles, the antigen or antibody is introduced into the surface of the latex particles when the synthesis is completed, and as a result, the removal of the unbound antigen or antibody from the latex particles by washing or the peeling of the bound antigen or antibody from the latex particles by centrifugation or dispersion, which occurs in latex particles produced by conventional methods, can be avoided. Further, a high reactivity can be obtained by using such latex particles. Furthermore, because the antigen or antibody is introduced into the surface of the latex particles when the synthesis is completed, the denaturation due to steric hindrance by the binding does not occur, and therefore, a reaction with a sample in which a nonspecific reaction is observed when conventional latex particles are used can be avoided.

In the process of the present invention, a mechanism of the introduction of the coexisting antigen or antibody into the surface of the polymer particles (for example, latex) in miniemulsion polymerization is not clarified, but the present inventors suppose the following mechanism. That is, the antigen or antibody used in the present invention exhibits a surface activity, and therefore, it is considered that the antigen or antibody exists on the surface of the polymer particles (for example, latex), as an interface with water, due to the hydrophilic portion. In this regard, the present invention is not limited to the supposition.

The present invention relates to a novel agent for immunological analysis and a novel method for immunological analysis. In the agent and method for immunological analysis of the present invention, latex particles having an antigen or antibody (i.e., an immunological partner) introduced into the surface of the latex particles (partner-introduced latex particles) are used, instead of conventional latex particles carrying an antigen or antibody on the surface thereof by a physical or chemical binding. The partner-introduced latex particles are not particularly limited, so long as the antigen or antibody is carried on the surface of the latex particles by embedding part of the antigen or antibody into the latex particles. The partner-introduced latex particles can be produced by the process of the present invention.

In the present invention, a latex method (a latex agglutination method or a B/F separation using latex) is used to perform analysis. In a system where latex particles into which an antigen or antibody specific to a substance to be analyzed is introduced are brought into contact with the substance to be analyzed (i.e., a system where an antigen-antibody reaction on the latex is carried out), denaturation due to steric hindrance does not occur in the introduced antigen or antibody, and therefore, the latex particles do not react with a sample nonspecific to the denatured portion, and as a result, the substance to be analyzed can be analyzed (detected or measured, preferably measured) at a higher sensitivity, in comparison with conventional methods.

A substance which may be analyzed by the present invention (a substance to be analyzed) is not particularly limited, so long as it can be analyzed as an antigen or an antibody by generally utilizing an antigen-antibody reaction, and physiologically active substances are preferable. Examples of the substance to be analyzed include proteins, lipids, and sugar chains, more particularly, IgG, C-reactive protein (CRP), ferritin, β-2 microglobulin, α-fetoprotein (AFP), IgE, hepatitis B virus (HBs antibody or HBc antibody), D dimer, fibrin/fibrinogen degradation product (FDP), soluble fibrin (SF), plasmin-α2-plasmin inhibitor complex (PPI), prostate specific antigen (PSA), elastase 1, elastase XDP, thrombomodulin, and albumin (preferably serum albumin).

A sample which may be analyzed by the present invention is not particularly limited, so long as it is suspected of containing the above substance to be analyzed. The sample may be, particularly, biological samples, such as blood, serum, plasma, urine, cerebrospinal fluid, cell extracts, or disrupted tissue liquids.

In the present invention, a latex method is used to perform analysis. In the latex method of the present invention, latex particles into which an antigen or antibody specific to a substance to be analyzed is introduced are used.

An average particle size of the partner-introduced latex particles may be appropriately selected in accordance with a detection concentration of the substance to be analyzed, or a measurement apparatus. The average particle size can be appropriately selected within a range of generally 0.05 to 0.5 μm.

As the antibody introduced into latex particles, a monoclonal antibody or a polyclonal antibody may be used. The antibody may be used as an immunoglobulin molecule per se, or a fragment thereof, such as Fab, Fab', F(ab')$_2$, or Fv.

The agent for immunological analysis of the present invention may be prepared in various forms, for example, a one-reagent-component system containing a buffer and the latex particles into which an antigen or antibody is introduced; a two-reagent-components system in which the first reagent contains a buffer and the second reagent contains a monoclonal antibody and the latex particles into which an antigen or antibody is introduced; or a two-reagent-components system in which the first reagent contains a buffer and the introduced latex particles and the second reagent contains latex particles sensitized with an antigen or antibody.

In the method of the present invention, the above reagent(s) are used to carry out an agglutination reaction, and a degree of the agglutination is optically analyzed (particularly measured) to analyze (particularly measure) an amount of the substance to be analyzed contained in a sample. The optical analysis of a degree of the latex-particles-agglutination may be carried out by, for example, an optical instrument for measuring an intensity of a scattered light, an absorbance, or an intensity of a transmitted light. A preferred measuring wavelength is 300 to 800 nm. The degree of agglutination may be carried out, in accordance with a known method, by selecting a size (average particle size) of the latex particle, a latex particle concentration, or a reaction time, and measuring an increase or decrease in an intensity of a scattered light, an absorbance, or an intensity of a transmitted light, or a combination thereof.

Alternatively, an amount of the substance to be analyzed contained in a sample can be analyzed (particularly measured), by bringing the above reagent(s) into contact with a sample in a liquid, carrying out a B/F separation to separate the latex particles from the liquid, and analyzing (particularly measuring) the substance to be analyzed bound to the latex particles, or the substance to be analyzed remaining in the liquid.

In the present invention, the latex-particles-agglutination reaction may be measured more accurately, a measurable range in a low concentration may be extended, and a nonspecific reaction may be avoided, by not only selecting the type of an antigen or antibody to be introduced, but also adjusting other factors which may affect the latex agglutination reaction. As the factors, there may be mentioned, for example, a concentration of latex particles, an amount of an antibody introduced into the latex particles, or a particle size of the latex particle.

The antigen-antibody reaction used in the present invention may be carried out under the same conditions as those in a conventional antigen-antibody reaction. As a reaction medium, various buffers may be appropriately selected in accordance with the type of the substance to be analyzed. An ionic strength and a pH of the buffer are not particularly limited, so long as the buffer does not inactivate the substance to be analyzed and does not inhibit the antigen-antibody reaction. As the buffer, for example, a Good's buffer, a glycine buffer, or a tris buffer may be used. The pH in the reaction is preferably 5 to 10, more preferably 6 to 8. The reaction temperature is preferably 0 to 50° C., more particularly 20 to 40° C. The reaction time may be appropriately selected.

EXAMPLES

The present invention will now be further illustrated by, but is by no means limited to, the following Examples.

Example 1

Preparation of Reagent for Measuring Anti-Bovine Serum Albumin (BSA) Antibody (1) Preparation of BSA-Introduced Latex Particles After 40 mmol of styrene, 4 mmol of hexadecane, 200 mg of BSA, 0.8 mmol of $CH_2=C(CH_3)COO(CH_2CH_2O)_{23}CH_3$ (NK ester M-230G; Shin-nakamura Chemical Co. Ltd.), 0.4 mmol of ascorbic acid, and 20 g of water were mixed, the mixture was sonicated [output: 80%, pulse: 50%, UH-300 (SMT Co., Ltd.)] in an ice bath for 15 minutes. The whole was transferred to a three-necked flask, and nitrogen gas was bubbled through the whole for 15 minutes while stirring at 100 rpm. Further, 0.4 mmol of $H_2O_2$ was added, and polymerized at 30° C. or 60° C. for 6 hours while stirring at 200 rpm to prepare BSA-introduced latex particles. The average particle sizes of the resulting BSA-introduced latex particles were 0.109 μm (polymerization at 30° C.) and 0.121 μm (polymerization at 60° C.).

(2) Preparation of Suspension of BSA-Introduced Latex Particles

With respect to 1 mL of the BSA-introduced latex particles (concentration: 1%), 1 mL of a blocking reagent for immunological measurement N101 (NOF Corporation) was added, and stirred at room temperature for 30 minutes. This mixture was centrifuged at 35000 rpm. The resulting precipitate (i.e., latex) was suspended in 10 mL of a Tris buffer (pH 8.0) to prepare a suspension of BSA-introduced latex particles.

(3) Preparation of Buffer

Sodium chloride was added to a 0.1 moL/L Tris buffer (pH 8.0) containing 0.5 wt % of BSA so as to become a concentration of 0.9 wt % to prepare a buffer. Hereinafter, an NaCl-containing Tris buffer without BSA is referred to as "buffer A", and an NaCl-containing Tris buffer with BSA is referred to as "buffer B".

(4) Reagent for Measuring Anti-BSA Antibody

A two-reagent-components system consisting of the suspension of BSA-introduced latex particles (second reagent) prepared in Example 1(2) and buffer A or B (first reagent) prepared in Example 1(3) was evaluated in the following examples, as a reagent for measuring an anti-BSA antibody, a reagent for immunological analysis of the present invention.

Example 2

Measurement of Standard Solution of Anti-BSA Antibody (1) Preparation of Standard Solution of Anti-BSA Antibody An anti-BSA antibody (Rabbit Anti cow albumin; DAKO, 900 units) was serially diluted twofold with physiological saline to prepare a series of serial dilutions of a standard anti-BSA antibody having concentrations of 900, 450, 225, 113, 56, 28, 14, and 7 units.

(2) Measurement of Standard Solution of Anti-BSA Antibody

After 90 μL of buffer A or B prepared in Example 1(3) was mixed with 15 μL of each of the dilution series, and incubated at 37° C. for a predetermined period of time, 90 μL of the suspension of BSA-introduced latex particles prepared in Example 1(2) was further added and stirred. From the last addition, absorbances at wavelengths of 800 nm and 570 nm were measured for 5 minutes. The difference between a variation of absorbance (i.e., an amount of change in absorbance) at 570 nm and a variation of absorbance at 800 nm was regarded as a variation of absorbance ($\Delta$Abs). The measurement was carried out using an automated analyzer (Hitachi 7170, Hitachi Ltd.).

For comparison, polystyrene latex particles having an average particle size of 0.11 μm (JSR Corporation, solid content: 10%) were used to prepare a suspension of BSA-bound latex particles by sensitizing 1 mL of the particles (concentration: 1%) with 0.3% (3 mg/mL) of BSA.

The results are shown in Table 1 and FIG. 1, and Table 2. Table 1 and FIG. 1 show the results of the reagent (polymerization temperature=30° C.) of the present invention described in Example 1(4) using buffer A or B, as well as the results of a conventional reagent. Table 2 shows the results of the reagents (polymerization temperature=30° C. or 60° C.) of the present invention described in Example 1(4) using buffer A (i.e., without BSA), as well as the results of a conventional reagent.

As apparent from Table 1 and FIG. 1, when buffer A (i.e., without BSA) was used, the suspension of BSA-introduced latex particles (reagent of the present invention) showed a variation of absorbance ($\Delta$Abs) of 24513 at an anti-BSA antibody concentration of 900 units, whereas the suspension of BSA-bound latex particles (conventional reagent) showed a variation of absorbance ($\Delta$Abs) of 385 at an anti-BSA antibody concentration of 900 units, and therefore, the suspension of BSA-introduced latex particles apparently exhibited a higher sensitivity. When buffer B (i.e., with 0.5% BSA) was used, no reaction with the dilution series of the anti-BSA antibody was observed using either suspension.

TABLE 1

| Anti-BSA antibody | Variation of absorbance ($\Delta$Abs) | | | |
|---|---|---|---|---|
| | Conventional reagent BSA-bound particles | | Reagent of the invention BSA-introduced particles | |
| (titer) | buffer A | buffer B | buffer A | buffer B |
| 0 | −20 | −10 | −102 | −50 |
| 7 | −38 | −7 | 84 | −50 |
| 14 | −19 | −7 | 407 | −48 |
| 28 | −19 | −9 | 1439 | −46 |
| 56 | −18 | −6 | 4546 | −45 |
| 113 | −15 | −6 | 7024 | −48 |
| 225 | −5 | −2 | 11471 | −49 |
| 450 | 63 | 2 | 16397 | −43 |
| 900 | 385 | 11 | 24513 | −46 |

As apparent from Table 2, when the suspensions of BSA-introduced latex particles (reagent of the present invention) were used, the suspension of BSA-introduced latex particles obtained by carrying out the polymerization reaction at a low temperature (30° C.) showed a variation of absorbance ($\Delta$Abs) of 24513 at an anti-BSA antibody concentration of 900 units, whereas the suspension of BSA-introduced latex particles obtained by carrying out the polymerization reaction at a high temperature (60° C.) showed a variation of absorbance ($\Delta$Abs) of 8480 at an anti-BSA antibody concentration of 900 units, and therefore, the suspension of BSA-introduced latex particles prepared at low temperature exhibited a higher sensitivity. Further, the suspension of BSA-bound latex particles (conventional reagent) showed a variation of absorbance ($\Delta$Abs) of 385 at an anti-BSA antibody concentration of 900 units, and therefore, the suspensions of BSA-introduced latex particles apparently exhibited a higher sensitivity.

TABLE 2

| Anti-BSA antibody | Variation of absorbance ($\Delta$Abs) | | |
|---|---|---|---|
| | | BSA-introduced particles Polymerization temp. | |
| (titer) | BSA-bound particles | 30° C. | 60° C. |
| 0 | −20 | −102 | −73 |
| 14 | −19 | 407 | −55 |
| 28 | −19 | 1439 | −1 |
| 56 | −18 | 4546 | 114 |
| 113 | −15 | 7024 | 406 |
| 225 | −5 | 11471 | 1169 |
| 450 | 63 | 16397 | 3507 |
| 900 | 385 | 24513 | 8480 |

Example 3

Measurement of Human Sera Using Reagent for Measuring Anti-BSA Antibody

In this Example, the procedures described in Example 2(2) were repeated, except that five human serum samples (Nos. 1 to 5) as normal samples and three human serum samples (Nos. 6 to 8) as nonspecific samples were used instead of the dilution series of a standard anti-BSA antibody. The nonspecific samples nonspecifically reacted with a suspension of latex particles to which BSA was bound (i.e., BSA-bound latex particles), but did not react with a suspension of latex particles to which BSA was not bound.

The results are shown in Table 3.

As shown in Table 3, the normal serum samples (Nos. 1 to 5) and the nonspecific serum samples (Nos. 6 to 8) did not react with the suspension of BSA-introduced latex particles. However, the suspension of BSA-bound latex particles strongly reacted with the nonspecific samples when the buffer without BSA (buffer A) or the buffer in which 0.5% BSA was suspended (buffer B) was used.

TABLE 3

| Human serum samples | Variation of absorbance (ΔAbs) | | | |
|---|---|---|---|---|
| | Conventional reagent BSA-bound particles | | Reagent of the invention BSA-introduced particles | |
| | buffer A | buffer B | buffer A | buffer B |
| [Normal] | | | | |
| No. 1 | −76 | −54 | −4 | 2 |
| No. 2 | −88 | 25 | −31 | −16 |
| No. 3 | 53 | 63 | −47 | −39 |
| No. 4 | 89 | 92 | −5 | 16 |
| No. 5 | 100 | 129 | 2 | 14 |
| [Nonspecific] | | | | |
| No. 6 | 6382 | 6463 | 20 | 60 |
| No. 7 | 2536 | 3570 | 23 | 71 |
| No. 8 | 1571 | 2317 | 13 | 74 |

Example 4

Preparation of Reagent for Measuring Anti-IgG (1) Preparation of IgG-Introduced Latex Particles After 40 mmol of styrene, 4 mmol of hexadecane, 200 mg of IgG, 0.6 mmol of $CH_2=C(CH_3)COO(CH_2CH_2O)_{23}CH_3$ (NK ester M-230G; Shin-nakamura Chemical Co. Ltd.), 0.4 mmol of ascorbic acid, and 20 g of water were mixed, the mixture was sonicated [output: 80%, pulse: 50%, UH-300 (SMT Co., Ltd.)] in an ice bath for 15 minutes. The whole was transferred to a three-necked flask, and nitrogen gas was bubbled through the whole for 15 minutes while stirring at 100 rpm. Further, 0.4 mmol of $H_2O_2$ was added, and polymerized at 30° C. for 6 hours while stirring at 200 rpm to prepare IgG-introduced latex particles. The average particle sizes of the resulting IgG-introduced latex particles were 0.318 μm.

(2) Preparation of Suspension of IgG-Introduced Latex Particles

With respect to 1 mL of the IgG-introduced latex particles (concentration: 1%), 1 mL of a blocking reagent for immunological measurement N101 (NOF Corporation) was added, and stirred at room temperature for 30 minutes. This mixture was centrifuged at 35000 rpm. The resulting precipitate (i.e., latex) was suspended in 10 mL of a Tris buffer (pH 8.0) to prepare a suspension of IgG-introduced latex particles.

(3) Reagent for Measuring Anti-IgG Antibody

A two-reagent-components system consisting of the suspension of IgG-introduced latex particles (second reagent) prepared in Example 4(2) and buffer B (first reagent) prepared in Example 1(3) was evaluated in the following examples, as a reagent for measuring an anti-IgG antibody, a reagent for immunological analysis of the present invention.

Example 5

Measurement of Standard Solution of Anti-IgG Antibody (1) Preparation of Standard Solution of Anti-IgG Antibody An anti-IgG antibody (Anti-IgG H&L chains; MILES-YEDA, 2.8 mg/mL) was serially diluted twofold with physiological saline to prepare a series of seven serial dilutions of a standard anti-IgG antibody having concentrations of 2.8, 1.4, 0.7, 0.35, 0.175, 0.088, and 0.044 mg/mL.

(2) Measurement of Standard Solution of Anti-IgG Antibody

After 90 μL of the buffer prepared in Example 1(3) was mixed with 2 μL of each of the dilution series, and incubated at 37° C. for a predetermined period of time, 90 μL of the suspension of IgG-introduced latex particles prepared in Example 4(2) was further added and stirred. From the last addition, absorbances at wavelengths of 800 nm and 570 nm were measured for 5 minutes. The difference between a variation of absorbance at 570 nm and a variation of absorbance at 800 nm was regarded as a variation of absorbance (ΔAbs). The measurement was carried out using an automated analyzer (Hitachi 7170, Hitachi Ltd.).

For comparison, polystyrene latex particles having an average particle size of 0.283 μm (Sekisui, solid content: 10%) were used to prepare a suspension of IgG-bound latex particles by sensitizing 1 mL of the particles (concentration: 1%) with 1% (10 mg/mL) of IgG, and the resulting suspension of IgG-bound latex particles and a suspension of latex particles not sensitized with IgG were used.

Figure 2:
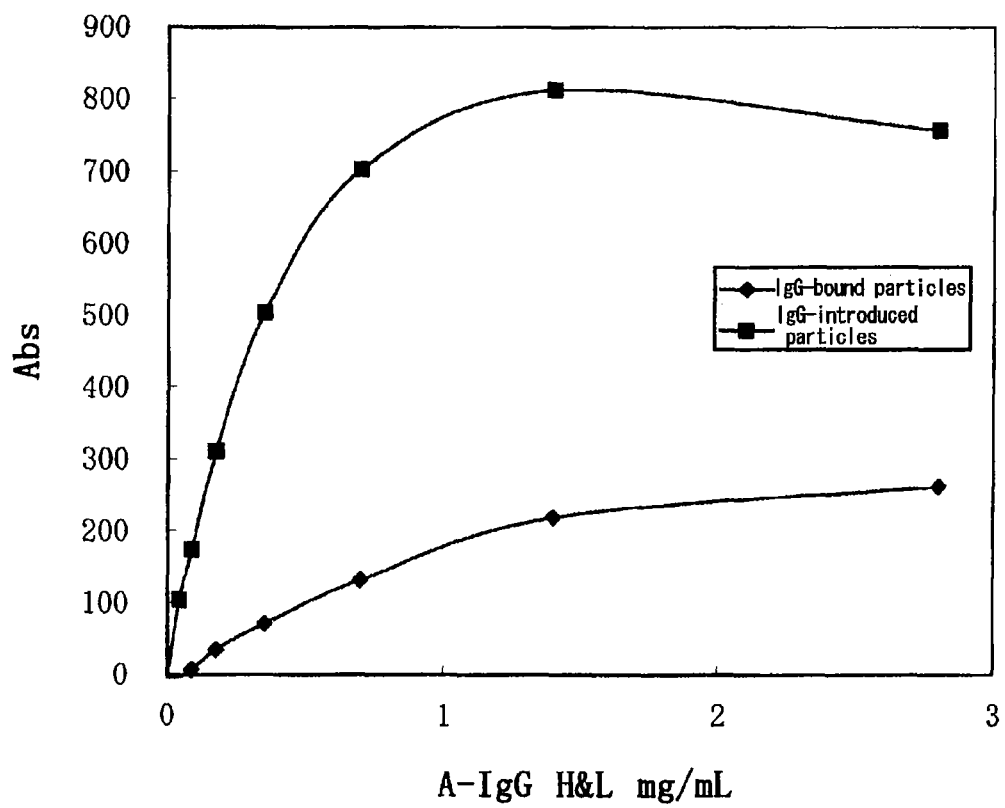
FIG. 2 is a graph showing the results obtained by measuring two-fold serial dilutions of a standard solution of an anti-IgG antibody, using a reagent of the present invention containing BSA-introduced latex particles, or a conventional reagent containing BSA-bound latex particles.

The results of the reagent of the present invention described in Example 4(3) are shown in Table 4 and FIG. 2, together with the results of the conventional reagent.

As apparent from Table 4 and FIG. 2, the suspension of IgG-introduced latex particles (reagent of the present invention) showed a variation of absorbance (ΔAbs) of 812 at an anti-IgG antibody concentration of 1.4 mg/mL, whereas the suspension of IgG-bound latex particles (conventional reagent) showed a variation of absorbance (ΔAbs) of 219, and therefore, the suspension of IgG-introduced latex particles apparently exhibited a higher sensitivity.

TABLE 4

| Anti-IgG antibody (mg/mL) | Variation of absorbance (ΔAbs) | | |
|---|---|---|---|
| | Reagent of the invention | Conventional reagent | |
| | BSA-introduced particles | BSA-bound particles | Unbound particles |
| 0 | −1 | −4 | −12 |
| 0.044 | 104 | −3 | −8 |
| 0.088 | 174 | 7 | −5 |
| 0.175 | 311 | 35 | −4 |
| 0.35 | 504 | 71 | −6 |
| 0.7 | 703 | 132 | −2 |
| 1.4 | 812 | 219 | −5 |
| 2.8 | 757 | 262 | −5 |

Example 6

Preparation of Anti-CRP-Antibody-F(ab')$_2$-Introduced Measuring Reagent (1) Preparation of Anti-CRP-Antibody-F(ab')$_2$-Introduced Latex Particles After 10 mmol of styrene, 1 mmol of hexadecane, 50 mg of anti-CRP antibody F(ab')$_2$, 0.2 mmol of CH$_2$=C(CH$_3$)COO(CH$_2$CH$_2$O)$_{23}$CH$_3$ (NK ester M-230G; Shin-nakamura Chemical Co. Ltd.), 0.1 mmol of ascorbic acid, and 5 g of water were mixed, the mixture was sonicated [output: 50%, pulse: 50%, UH-300 (SMT Co., Ltd.)] in an ice bath for 15 minutes. The whole was transferred to a three-necked flask, and nitrogen gas was bubbled through the whole for 15 minutes while stirring at 100 rpm. Further, 0.1 mmol of H$_2$O$_2$ was added, and polymerized at room temperature for 6 hours while stirring at 200 rpm to prepare anti-CRP-antibody-F(ab')$_2$- introduced latex particles. The average particle sizes of the resulting anti-CRP-antibody-F(ab')$_2$-introduced latex particles were 0.249 µm.

(2) Preparation of Suspension of Anti-CRP-Antibody-F(ab')$_2$-Introduced Latex Particles With respect to 1 mL of the anti-CRP-antibody-F(ab')$_2$-introduced latex particles (concentration: 1%), 1 mL of a blocking reagent for immunological measurement N101 (NOF Corporation) was added, and stirred at room temperature for 30 minutes. This mixture was centrifuged at 35000 rpm. The resulting precipitate (i.e., latex) was suspended in 10 mL of a Tris buffer (pH 8.0) to prepare a suspension of anti-CRP-antibody-F(ab')$_2$-introduced latex particles.

(3) Reagent for Measuring CRP

A two-reagent-components system consisting of the suspension of anti-CRP-antibody-F(ab')$_2$-introduced latex particles (second reagent) prepared in Example 6(2) and buffer B (first reagent) prepared in Example 1(3) was evaluated in the following examples, as a reagent for measuring CRP, a reagent for immunological analysis of the present invention.

Example 7

Measurement of Standard Solution of CRP (1) Preparation of Standard Solution of CRP CRP (Oriental Yeast Co., ltd., a recombinant CRP solution, 100 mg/dL) was serially diluted with physiological saline to prepare a series of six serial dilutions of a standard CRP having concentrations of 3.2, 1.6, 0.8, 0.4, 0.2, and 0.1 mg/dL.

(2) Measurement of Standard Solution of CRP

After 90 µL of the buffer prepared in Example 1(3) was mixed with 2 µL of each of the dilution series, and incubated at 37° C. for a predetermined period of time, 90 µL of the suspension of anti-CRP-antibody-F(ab')$_2$-introduced latex particles prepared in Example 6(2) was further added and stirred. From the last addition, absorbances at wavelengths of 800 nm and 570 nm were measured for 5 minutes. The difference between a variation of absorbance at 570 nm and a variation of absorbance at 800 nm was regarded as a variation of absorbance (ΔAbs). The measurement was carried out using an automated analyzer (Hitachi 7170, Hitachi Ltd.).

The results of the reagent of the present invention described in Example 6(3) are shown in Table 5.

As apparent from Table 5, the suspension of anti-CRP-antibody-F(ab')$_2$-introduced latex particles (reagent of the present invention) showed a concentration-dependent reactivity with the CRP standard solutions in the range of 0.1 to 3.2 mg/dL.

TABLE 5

| CRP (mg/dL) | Variation of absorbance (ΔAbs) Reagent of the invention Anti-CRP-antibody-F(ab')$_2$-introduced particles |
|---|---|
| 0 | −36 |
| 0.1 | 6 |
| 0.2 | 57 |
| 0.4 | 154 |
| 0.8 | 315 |
| 1.6 | 482 |
| 3.2 | 533 |

INDUSTRIAL APPLICABILITY

The present invention can be applied to immunological analysis, particularly a latex agglutination method.

Although the present invention has been described with reference to specific embodiments, various changes and modifications obvious to those skilled in the art are possible without departing from the scope of the appended claims.

The invention claimed is:

1. A process for producing polymer particles having an antigen or an antibody incorporated into the surface thereof, comprising the step of carrying out miniemulsion polymerization using a monomer, a radical polymerization initiator, an emulsifier, and a hydrophobe in the presence of the antigen or antibody, wherein the radical polymerization initiator is a redox initiator.

2. The process of claim 1, wherein the miniemulsion polymerization is carried out at 0° to 60° C.

3. The process of claim 2, wherein the miniemulsion polymerization is carried out at 0° to 40° C.

4. The process of claim 1, wherein the redox initiator is a combination of ascorbic acid and H$_2$O$_2$.

5. The process according to claim 1, wherein the emulsifier is a surfactant.

6. The process of claim 1, wherein the emulsifier is a polymeric surfactant having a polyethylene glycol chain.

7. The process of claim 1, wherein the hydrophobe is hexadecane or polystyrene.

* * * * *